US012746247B2

(12) United States Patent
Figadere et al.

(10) Patent No.: US 12,746,247 B2
(45) Date of Patent: Sep. 29, 2026

(54) TETRACYCLINE DERIVATIVES FOR TREATING NEURODEGENERATIVE OR NEUROINFLAMMATORY DISEASES

(71) Applicants: INSTITUT DU CERVEAU ET DE LA MOELLE EPINIERE, Paris (FR); INSTITUT NATIONAL DE LA SANTÉ ET DE LA RECHERCHE MÉDICALE, Paris (FR); CENTRE NATIONAL DE LA RECHERCHE SCIENTIFIQUE, Paris (FR); ASSISTANCE PUBLIQUE—HÔPITAUX DE PARIS, Paris (FR); SORBONNE UNIVERSITE, Paris (FR); UNIVERSITE PARIS-SACLAY, Gif-sur-Yvette (FR)

(72) Inventors: Bruno Figadere, Saint Cheron (FR); Rita Raisman-Vozari, Paris (FR); Patrick Pierre Michel, Paris (FR); Laurent Ferrie, Palaiseau (FR); Clémence Rose, Beziers (FR)

(73) Assignee: INSTITUT DU CERVEAU ET DE LA MOELLE EPINIERE, Paris (FR)

( * ) Notice: Subject to any disclaimer, the term of this patent is extended or adjusted under 35 U.S.C. 154(b) by 595 days.

(21) Appl. No.: 18/031,632

(22) PCT Filed: Oct. 14, 2021

(86) PCT No.: PCT/EP2021/078525

§ 371 (c)(1),
(2) Date: Apr. 13, 2023

(87) PCT Pub. No.: WO2022/079204

PCT Pub. Date: Apr. 21, 2022

(65) Prior Publication Data

US 2023/0390309 A1 Dec. 7, 2023

(30) Foreign Application Priority Data

Oct. 14, 2020 (EP) .................................... 20306201

(51) Int. Cl.

*A61K 31/65* (2006.01)
*A61P 25/28* (2006.01)
*C07C 231/12* (2006.01)
*C07C 235/84* (2006.01)

(52) U.S. Cl.

CPC ............. *A61K 31/65* (2013.01); *A61P 25/28* (2018.01); *C07C 231/12* (2013.01); *C07C 235/84* (2013.01); *C07C 2603/46* (2017.05)

(58) Field of Classification Search

CPC ..................................................... A61K 31/65

See application file for complete search history.

(56) References Cited

U.S. PATENT DOCUMENTS

| | | | |
|---|---|---|---|
| 3,188,348 | A | 6/1965 | Butler et al. |
| 2003/0114426 | A1 | 6/2003 | Pflugfelder et al. |
| 2011/0230452 | A1 | 9/2011 | Sucholeiki |

FOREIGN PATENT DOCUMENTS

| | | | |
|---|---|---|---|
| CA | 2476792 | A1 | 10/2003 |
| CN | 1481801 | A | 3/2004 |
| EP | 1829546 | A1 | 9/2007 |
| WO | WO 2004/064728 | | 8/2004 |
| WO | 2012118498 | A1 | 9/2012 |
| WO | 2020206321 | A1 | 10/2020 |

OTHER PUBLICATIONS

Written Opinion in International Application No. PCT/EP2021/078525, Jan. 5, 2022, pp. 1-5.

Kende, A. S. et al. "Total Synthesis of Tetracyclines. IV. Synthesis of an Anhydrotetracycline Derivative" *Journal of the American Chemical Society*, Jan. 20, 1961, pp. 439-449, vol. 83, No. 2.

Stephens, C. R. et al. "Terramycin. VIII. Structure of Aureomycin and Terramycin" *Journal of the American Chemical Society*, Oct. 5, 1952, pp. 4976-4977, vol. 74, No. 19.

Bortolanza, M. et al. "Tetracycline repurposing in neurodegeneration: focus on Parkinson's disease", J. Neural. Transm., 2018, pp. 1403-1415, vol. 125.

González-Lizárraga, F. et al. "Repurposing doxycycline for synucleinopathies: remodelling of a α-synuclein oligomers towards non-toxic parallel beta-sheet structured species", Sci. Rep., Feb. 3, 2017, pp. 1-13, vol. 7.

Guerreiro, S. et al. "Protection of midbrain dopaminergic neurons by the end-product of purine metabolism uric acid: potentiation by low-level depolarization", J Neurochem., 2009, pp. 1118-1128, vol. 109, No. 4.

Rousseau, E. et al. "The Iron-Binding Protein Lactoferrin Protects Vulnerable Dopamine Neurons from Degeneration by Preserving Mitochondrial Calcium Homeostasis", Mol. Pharmacol., Dec. 2013, pp. 888-898, vol. 84, No. 6.

Lavaur, J. et al. "The noble gas xenon provides protection and trophic stimulation to midbrain dopamine neurons", J Neurochem., 2017, pp. 14-28, vol. 142, No. 1.

*Primary Examiner* — John S Kenyon

(57) ABSTRACT

The present invention relates to the field of medicine. In particular, it relates to the use of tetracycline derivatives in the treatment or prevention of a neurodegenerative or neuroinflammatory disease, such as Parkinson's disease.

14 Claims, 2 Drawing Sheets

TETRACYCLINE DERIVATIVES FOR TREATING NEURODEGENERATIVE OR NEUROINFLAMMATORY DISEASES

CROSS-REFERENCE TO RELATED APPLICATION

This application is the U.S. national stage application of International Patent Application No. PCT/EP2021/078525, filed Oct. 14, 2021.

TECHNICAL FIELD

The present invention relates to the field of medicine. In particular, it relates to the use of tetracycline derivatives in the treatment or prevention of a neurodegenerative or neuroinflammatory disease, such as Parkinson's disease.

TECHNICAL BACKGROUND

The aggregation of the protein α-synuclein into amyloid fibrils contributes critically to the pathogenesis of synucleinopathies, a group of neurodegenerative diseases comprising Parkinson's disease and other related disorders. In the pathological brain but also elsewhere in the body, in particular in the gut, α-synuclein accumulates in proteinaceous aggregates called Lewy bodies or Lewy neurites that disrupt normal function of specific subpopulations of nerve cells and cause their demise. In vitro studies have shown that human recombinant α-synuclein may polymerize into amyloid fibrils resembling those found in Lewy bodies. This suggests that drugs having the ability to prevent α-synuclein amyloid aggregation may be of interest for the treatment of synucleinopathies.

A wide range of tetracycline derivatives has been described for treating synucleopathies, and more broadly neurodegenerative diseases.

For instance, WO 2004/064728 discloses specific tetracycline derivatives and their use for treating diseases or conditions involving underlying inflammatory processes, including among others, neurological disorders such as multiple sclerosis, Parkinson's disease, Huntington's disease, or Alzheimer's disease.

Also, CN1481801 discloses tetracycline derivatives and their use in the treatment of Parkinson's disease and other neurodegenerative diseases where nitric oxide is involved, such as Alzheimer's disease, multiple sclerosis, Huntington's disease, or Lewy body disease. Bortolanza et al. (J. Neural. Transm. 2018, 125, 1403-1415) and Gonzalez-Lizarraga et al. (Sci. Rep. 2017, 7, 41755) have reported that doxycycline, which is a tetracycline derivative, has the ability to inhibit amyloid aggregation of α-synuclein.

However, the antibacterial activity of tetracyclines like doxycycline represents a potential hurdle for the treatment of neurodegenerative diseases, and in particular synucleinopathies, because chronic treatments needed for these pathologies might favor the emergence of antibiotic-resistant pathogenic bacteria.

Thus, there remains a need to develop tetracycline derivatives having anti-α-synuclein-aggregation properties and a limited or no antibiotic activity.

SUMMARY OF THE INVENTION

In this respect, the inventors have developed derivatives of chlortetracycline, which overcome the above deficiencies. Indeed, the inventors have demonstrated that, while inhibiting amyloid aggregation of α-synuclein, more efficiently than doxycycline, these compounds display a highly limited or no antibiotic activity. These compounds appear therefore as particularly well-suited for treating or preventing synucleinopathies such as Parkinson's disease, and more broadly, neurodegenerative or neuroinflammatory diseases.

Hence, the present invention relates to a compound represented by the following formula (I):

(I)

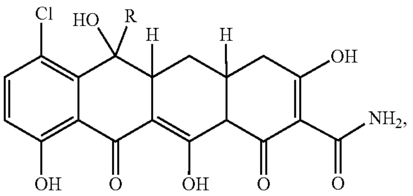

wherein R is a hydrogen atom or a methyl group, or a pharmaceutically acceptable salt or solvate thereof, for use in the treatment or prevention of a neurodegenerative or neuroinflammatory disease, preferably a synucleinopathy, more preferably Parkinson's disease.

It also relates to a pharmaceutical composition comprising a compound of formula (I) as defined herein, or a pharmaceutically acceptable salt or solvate thereof, and at least one pharmaceutically acceptable excipient, for use in the treatment or prevention of a neurodegenerative or neuroinflammatory disease, preferably a synucleinopathy, more preferably Parkinson's disease.

Another object of the invention is a compound of formula (I-H):

(I-H)

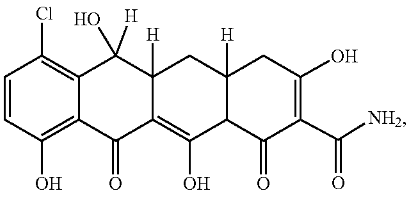

or a pharmaceutically acceptable salt thereof, for use as a medicine.

A further object of the invention is a pharmaceutical composition comprising a compound of formula (I-H):

(I-H)

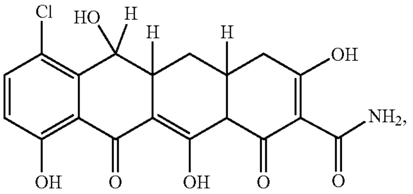

or a pharmaceutically acceptable salt or solvate thereof, and at least one pharmaceutically acceptable excipient.

The invention also relates to a process for preparing a compound of formula (I):

(I)

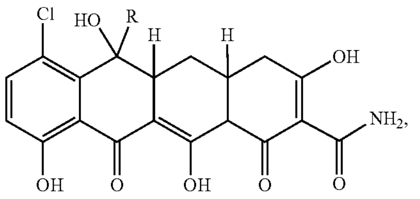

wherein R is a hydrogen atom or a methyl group, said process comprising the steps of:

(a) contacting a compound of formula (III) with an acid $H^+$, $X^-$ wherein $X^-$ is an anion, (III)

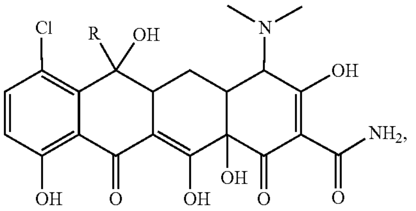

wherein R is a hydrogen atom or a methyl group, so as to obtain a compound of formula (II):

(II)

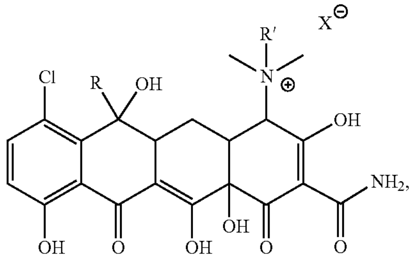

wherein R is a hydrogen atom or a methyl group,

R' is a hydrogen atom, and $X^-$ is an anion;

(b) reacting said compound of formula (II) with a reducing system.

The invention further relates to a process for preparing a compound of formula (I):

(I)

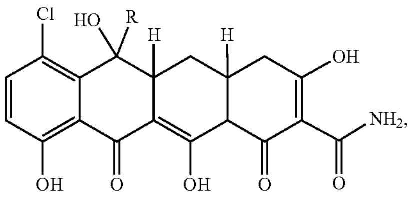

wherein R is a hydrogen atom or a methyl group, said process comprising the step of:

(b) reacting a compound of formula (II) with a reducing system:

(II)

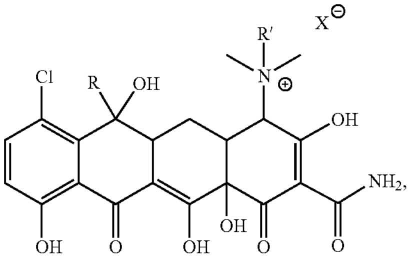

wherein R is a hydrogen atom or a methyl group,

R' is a methyl group, and $X^-$ is an anion.

DETAILED DESCRIPTION OF THE INVENTION

Definitions

Figure 1:
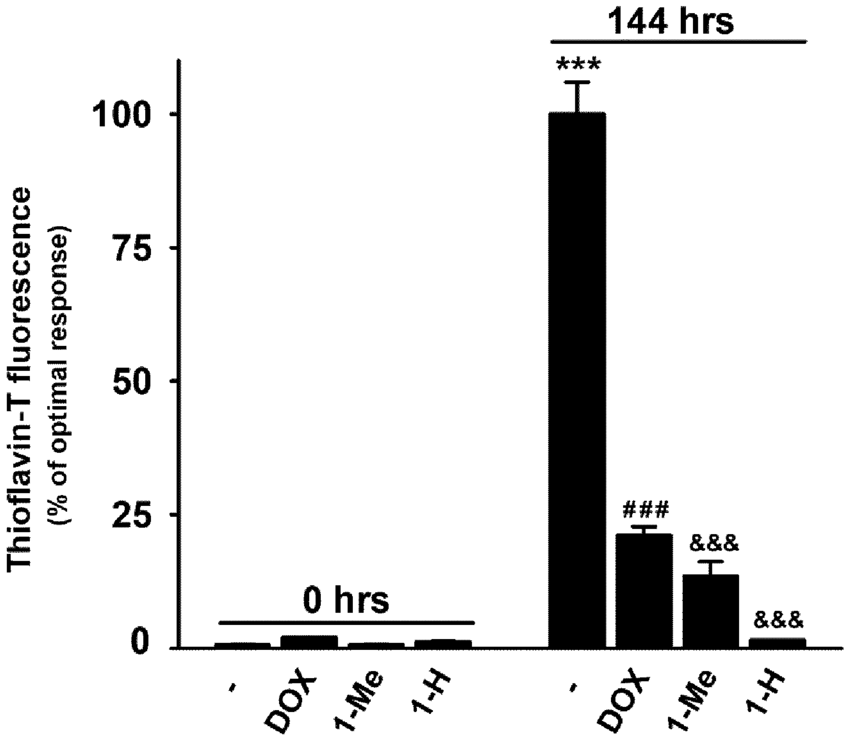
FIG. 1: Assessment of the impact of compounds (1-Me), (1-H) and doxycycline (DOX) on α-Synuclein amyloid aggregation in vitro by a thioflavin-T assay. All tetracyclines derivatives were tested at 100 μM. Data are expressed in percent of the optimal response after 144 hrs of shaking. Error bars indicate mean values±SD (n=3). One-way ANOVA followed by Student-Newman-Keuls post-hoc test; ***p<0.001 vs no tetracycline at 0 hrs; $^{\#\#\#}$p<0.001 vs no tetracycline at 144 hrs; $^{\&\&\&}$p<0.001 vs DOX at 144 hrs.

As used herein, the terms "treatment", "treat" or "treating" refer to any act intended to ameliorate the health status of patients such as therapy, prevention, prophylaxis and retardation of a disease. In certain embodiments, such terms refer to the amelioration or eradication of the disease, or symptoms associated with it. In other embodiments, this term refers to minimizing the spread or worsening of the disease, resulting from the administration of one or more therapeutic agents to a subject with such a disease. The term "treatment" or "treating" also refers to delaying the onset of a disease or disorder.

As used herein, the terms "subject", "individual" or "patient" are interchangeable and refer to an animal, preferably to a mammal, even more preferably to a human, including adult, child, newborn or human at the prenatal stage. However, the term "subject" can also refer to non-human animals, in particular mammals such as dogs, cats, horses, cows, pigs, sheep or non-human primates, among others.

The terms "quantity," "amount," and "dose" are used interchangeably herein and may refer to an absolute quantification of a molecule.

As used herein, the terms "active principle", "active ingredient" and "active pharmaceutical ingredient" are equivalent and refers to a component of a pharmaceutical composition having a therapeutic effect.

As used herein, the term "therapeutic effect" refers to an effect induced by an active ingredient, or a pharmaceutical composition according to the invention, capable to prevent or to delay the appearance of a disease, or to cure or to attenuate the effects of a disease.

As used herein, the term "effective amount" refers to a quantity of an active ingredient or of a pharmaceutical composition which prevents, removes or reduces the deleterious effects of the disease. It is obvious that the quantity to be administered can be adapted by the man skilled in the art according to the subject to be treated, to the nature of the disease, etc. In particular, doses and regimen of administration may be function of the nature, of the stage and of the severity of the disease to be treated, as well as of the weight, the age and the global health of the subject to be treated, as well as of the judgment of the doctor.

As used herein, the term "excipient" or "carrier" refers to any ingredient except active ingredients that is present in a pharmaceutical composition. Its addition may be aimed to confer a particular consistency or other physical or gustative properties to the final product. An excipient or pharmaceutically acceptable carrier must be devoid of any interaction, in particular chemical, with the actives ingredients.

Compounds for Use

As illustrated by the examples, the inventors have demonstrated that the compounds of formula (I) have anti-aggregation properties, and limited or no antibiotic activity.

Accordingly, the present invention relates to a compound for use according to the present invention, said compound being represented by the following formula (I):

(I)

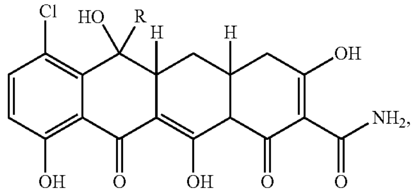

wherein R is a hydrogen atom or a methyl group, or a pharmaceutically acceptable salt or solvate thereof.

According to the present invention, a suitable pharmaceutically acceptable salt of a compound of the invention may be, for example, an acid-addition salt of a compound of the invention, such as, an acid-addition salt with an inorganic or organic acid, for example hydrochloric, hydrobromic, sulfuric, phosphoric, nitric, perchloric, acetic, trifluoroacetic, fumaric, formic, citric, maleic, propionic, succinic, glycolic, lactic, tartaric, palmoic, malonic, hydroxymaleic, phenylacetic, glutamic, benzoic, salicylic, toluenesulfonic, methanesulfonic, naphthalene-2-sulfonic, benzenesulfonic hydroxynaphthoic, hydroiodic, malic, steroic, or tannic acid. A suitable pharmaceutically acceptable salt of a compound of the invention may also be an alkali metal salt, for example a lithium, sodium or potassium salt, an alkaline earth metal salt, for example a calcium or magnesium salt, an ammonium salt or a salt with an organic base which affords a pharmaceutically acceptable cation, for example a salt with methylamine, dimethylamine, trimethylamine, piperidine, morpholine or tris-(2-hydroxyethyl)amine.

A "solvate", as used herein, refers to a complex comprising a compound of the invention with at least one solvent, typically a solvent in which the compound of the invention is reacted or from which it is precipitated or crystallized. For example, a complex with water is known as a "hydrate". Other examples of solvents which can be found in solvates include, but are not limited to, acetone, methyl ethyl ketone, toluene, methanol, ethanol, propanol, isopropanol, benzyl alcohol, acetonitrile, tetrahydrofuran, ether, or dichloromethane.

The compound of formula (I) may exist in the form of, or in equilibrium with, other tautomeric forms, for instance the following forms (not limitative):

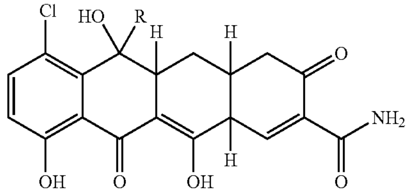

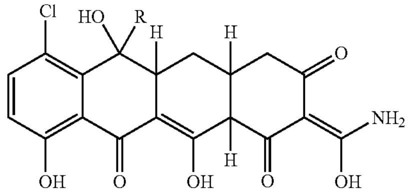

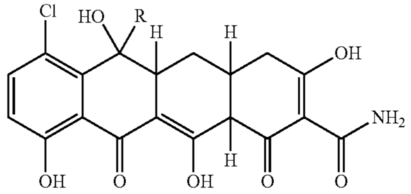

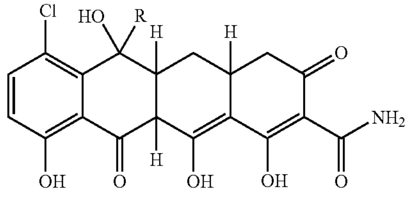

The present invention encompasses all tautomeric forms of the compound of formula (I).

The compound of formula (I) may exist in the form of one single enantiomer, one single diastereomer, a mixture of two or more diastereomers, or a mixture of two enantiomers (for instance, a racemate). The present invention encompasses all diastereomers and enantiomers of the compound of formula (I). Preferably, the compound of formula (I) exists in the form of one single enantiomer.

In a particular embodiment, a compound of formula (I) is of formula (1):

(1)

(1)

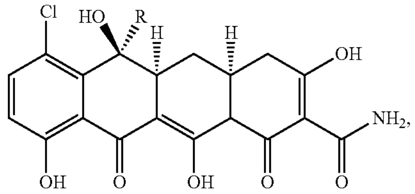

wherein R is a hydrogen atom or a methyl group, and/or its enantiomer.

In a more particular embodiment, a compound of formula (I) is of formula (1):

(1)

(1)

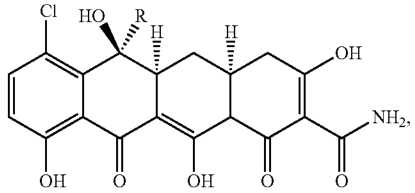

wherein R is a hydrogen atom or a methyl group.

In one embodiment, R is a methyl. A compound of formula (1) wherein R is a methyl is represented by the following formula (1-Me):

(1-Me)

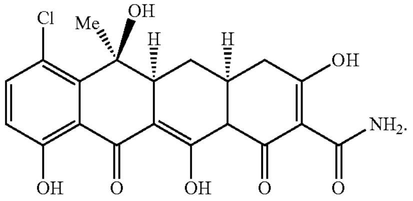

In another embodiment, R is a hydrogen atom. A compound of formula (1) wherein R is a hydrogen atom is represented by the following formula (1-H):

(1-H)

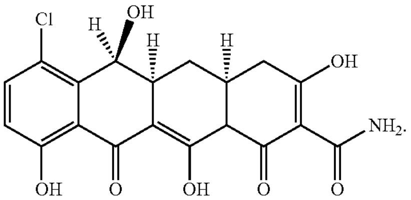

In a preferred embodiment, R is a hydrogen atom.

Another object of the invention is a compound of formula (I-H):

(I-H)

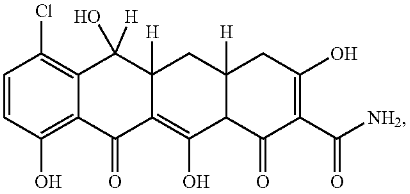

or a pharmaceutically acceptable salt thereof, for use as a medicine.

A further object of the invention is a pharmaceutical composition comprising a compound of formula (I-H):

(I-H)

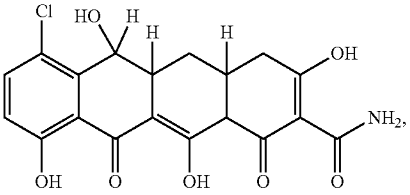

or a pharmaceutically acceptable salt or solvate thereof, and at least one pharmaceutically acceptable excipient.

Preferably, the compound of formula (I-H) is a compound of formula (1-H): and/or its enantiomer.

(1-H)

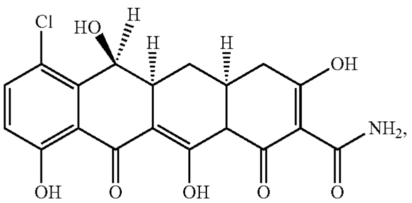

More preferably, the compound of formula (I-H) is a compound of formula (1-H):

(1-H)

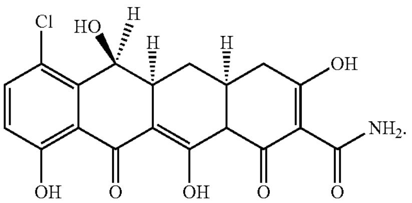

Pharmaceutical Compositions and Therapeutic Uses

The present invention also relates to a pharmaceutical composition comprising a compound of formula (I) as defined herein, or a pharmaceutically acceptable salt or solvate thereof, and at least one pharmaceutically acceptable excipient, for use according to the invention.

The invention also relates to a pharmaceutical composition comprising a compound of formula (I-H) as defined herein (preferably, of formula (1-H)), and at least one pharmaceutically acceptable excipient.

Compounds and pharmaceutical compositions of the present invention are particularly well-suited for use in the treatment and prevention of neurodegenerative or neuroinflammatory diseases.

As used herein, a "neurodegenerative disease" refers to a disease or a disorder which involves a progressive damage of the structure or function of a neuron, including the death or demyelination of the neuron.

As used herein, a "neuroinflammatory disease" refers to a disease or a disorder caused by an excessive inflammatory reaction of the nervous system.

According to the present invention, a neurodegenerative disease may also be a neuroinflammatory disease.

Examples of neurodegenerative and/or neuroinflammatory diseases include, but are not limited to, Alzheimer's disease, dementia associated with Alzheimer's disease (e.g. Pick's disease), Parkinson's disease, diffuse Lewy body disease, senile dementia, Huntington's disease, encephalitis, Gilles de la Tourette syndrome, multiple sclerosis, amyotrophic lateral sclerosis (ALS), advanced supranuclear paralysis, epilepsy, schizophrenia, depression, post-traumatic stress disorder, Lou Gehrig's disease, Creutzfeldt-Jakob disease, stroke, fragile X syndrome, multiple system atrophy (MSA), pure autonomic dysfunction with synuclein deposition (PAF), hereditary neurodegeneration with iron accumulation in the brain, accidental Lewy body disease in the elderly, Lewy body subtype Alzheimer's disease, Down syndrome, progressive supranuclear palsy, essential tremor with Lewy bodies, familial parkinsonism with or without dementia, tau and progranulin gene-related dementia with or without parkinsonism, bovine spongiform encephalopathy, secondary Parkinson's disease, parkinsonism resulting from neurotoxin exposure, drug-induced parkinsonism with α-synuclein deposition, and sporadic or hereditary spinocerebellar ataxia.

In a more particular embodiment, said neurodegenerative or neuroinflammatory disease is a synucleinopathy.

As used herein, a "synucleinopathy" refers to a neurodegenerative disease and/or a neuroinflammatory disease characterized by an abnormal accumulation of aggregates of alpha-synuclein protein in neurons, nerve fibers and/or glial cells.

Examples of synucleinopathy include, but are not limited to, Parkinson's disease, diffuse Lewy body disease (DLB), multiple system atrophy (MSA), pure autonomic dysfunction with synuclein deposition (PAF), hereditary neurodegeneration with iron accumulation in the brain, accidental Lewy body disease in the elderly, Lewy body subtype Alzheimer's disease, Down syndrome, essential tremor with Lewy bodies, familial parkinsonism with or without dementia, tau and progranulin gene-related dementia with or without parkinsonism, Creutzfeldt-Jakob disease, bovine spongiform encephalopathy, secondary Parkinson's disease, parkinsonism resulting from neurotoxin exposure, drug-induced parkinsonism with α-synuclein deposition, sporadic or hereditary spinocerebellar ataxia, and amyotrophic lateral sclerosis (ALS).

In a preferred embodiment, said neurodegenerative or neuroinflammatory disease is a synucleinopathy selected from the group consisting of Parkinson's disease, diffuse Lewy body disease, and multiple system atrophy.

More preferably, said synucleinopathy is Parkinson's disease.

The present invention also relates to a compound of formula (I) for use in inhibiting aggregation of α-synuclein protein, wherein said compound of formula (I) preferably has a limited or no antimicrobial activity.

As used herein, a "limited or no antimicrobial activity" refers to the antimicrobial activity of a compound of the invention having a minimal inhibitory concentration higher than 500 μM, preferably higher than 1000 μM, more preferably higher than 2000 μM, as measured by the disc diffusion method.

The invention further relates to a method for treating a disease in a subject, wherein a therapeutically effective amount of a compound of formula (I), preferably a compound of formula (I-H), is administered to said subject in need thereof, said disease being preferably a neurodegenerative or neuroinflammatory disease.

The present invention also relates to the use of a compound of formula (I), preferably a compound of formula (I-H), as a drug. The invention also relates to the use of a compound of formula (I), preferably a compound of formula (I-H), for the manufacture of a medicine.

In addition, the present invention relates to a method for treating a neurodegenerative or neuroinflammatory disease, preferably a synucleinopathy, more preferably Parkinson's disease, in a subject, wherein a therapeutically effective amount of a compound of formula (I), preferably a compound of formula (I-H), is administered to said subject suffering of said disease.

The invention also relates to the use of a compound of formula (I), preferably a compound of formula (I-H), for the manufacture of a medicine for the treatment of a neurodegenerative or neuroinflammatory disease, preferably a synucleinopathy, more preferably Parkinson's disease.

The human subject according to the invention may be a human at the prenatal stage, a new-born, a child, an infant, an adolescent or an adult, in particular an adult of at least 40 years old, preferably an adult of at least 50 years old, still more preferably an adult of at least 60 years old, even more preferably an adult of at least 70 years old.

In a preferred embodiment, the subject has been diagnosed with a disease and is in need of a treatment. Preferably, the subject has been diagnosed with a disease selected from a neurodegenerative or neuroinflammatory disease, preferably a synucleinopathy, more preferably Parkinson's disease.

In a particular embodiment, the subject presents a neurodegenerative or neuroinflammatory disease, preferably a synucleinopathy, more preferably Parkinson's disease.

Diagnostic method of these diseases are well known by the man skilled in the art.

The compound or the pharmaceutical composition of the present invention may be administered by any conventional route of administration. In particular, said compound or pharmaceutical composition can be administered by a topical, enteral, oral, parenteral, intranasal, intravenous, intraarterial, intramuscular, or subcutaneous administration and the like.

In particular, the compound or the pharmaceutical composition of the invention can be formulated for a topical, enteral, oral, parenteral, intranasal, intravenous, intra-arterial, intramuscular, or subcutaneous administration and the like.

Preferably, the compound of the invention or the pharmaceutical composition of the invention is administered by enteral or parenteral route of administration. When administered parenterally, the compound of the invention or the pharmaceutical composition of the invention is preferably administered by intravenous route of administration. When administered enterally, the compound of the invention or the pharmaceutical composition of the invention is preferably administered orally.

The pharmaceutical composition comprising the molecule is formulated in accordance with standard pharmaceutical practice (Lippincott Williams & Wilkins, 2000 and Encyclopedia of Pharmaceutical Technology, eds. J. Swarbrick and J. C. Boylan, 1988-1999, Marcel Dekker, New York) known by a person skilled in the art.

For oral administration, the composition can be formulated into conventional oral dosage forms such as tablets, gels, capsules, powders, granules and liquid preparations such as syrups, elixirs, and concentrated drops. Nontoxic solid carriers or diluents may be used which include, for example, pharmaceutical grades of mannitol, lactose, starch, magnesium stearate, sodium saccharine, talcum, cellulose, glucose, sucrose, magnesium, carbonate, and the like. For compressed tablets, binders, which are agents which impart cohesive qualities to powdered materials, are also necessary. For example, starch, gelatine, sugars such as lactose or dextrose, and natural or synthetic gums can be used as binders. Disintegrants are also necessary in the tablets to facilitate break-up of the tablet. Disintegrants include starches, clays, celluloses, algins, gums and crosslinked polymers. Moreover, lubricants and glidants are also included in the tablets to prevent adhesion to the tablet material to surfaces in the manufacturing process and to improve the flow characteristics of the powder material during manufacture. Colloidal silicon dioxide is most commonly used as a glidant and compounds such as talc or stearic acids are most commonly used as lubricants.

For transdermal administration, the composition can be formulated into ointment, cream or gel form and appropriate penetrants or detergents could be used to facilitate permeation, such as dimethyl sulfoxide, dimethyl acetamide and dimethylformamide.

Pharmaceutical compositions of the invention may be formulated to release the active drug substantially immediately upon administration or at any predetermined time or time period after administration.

Preferably, the treatment with the compound of the invention or the pharmaceutical composition of the invention start no longer than a month, preferably no longer than a week, once the disease is diagnosed. In a most preferred embodiment, the treatment starts within the month, within the week or the day of the diagnosis.

The dosages and dosage regimen in which the compounds of formula (I) are administered will vary according to the dosage form, mode of administration, the condition being treated and particulars of the patient being treated. It will be appreciated that the dosage of compounds of the present invention will vary from patient to patient not only for the particular compound or composition selected, the route of administration, and the ability of the compound (alone or in combination with one or more drugs) to elicit a desired response in the patient, but also factors such as disease state or severity of the condition to be alleviated, age, sex, weight of the patient, the state of being of the patient, and the severity of the pathological condition being treated, concurrent medication or special diets then being followed by the patient, and other factors which those skilled in the art will recognize, with the appropriate dosage ultimately being at the discretion of the attendant physician. Dosage regimens may be adjusted to provide the improved therapeutic response. A therapeutically effective amount is also one in which any toxic or detrimental effects of the compound or composition are outweighed by the therapeutically beneficial effects. Preferably, the compounds or compositions of the present invention are administered at a dosage and for a time such that the number and/or severity of the symptoms are decreased. The treatment may last as long as the disease persists.

The compound of the invention or the pharmaceutical composition of the invention may be administered as a single dose or in multiple doses.

Preferably, the treatment is administered regularly, preferably between every day and every month, more preferably between every day and every two weeks, more preferably between every day and every week, even more preferably the treatment is administered every day. In a particular embodiment, the treatment is administered several times a day, preferably at least 2 or 3 times a day, even more preferably at least 3 times a day.

The amount of compound of the invention or of pharmaceutical composition of the invention to be administered has to be determined by standard procedure well known by those of ordinary skills in the art. As mentioned above, physiological data of the patient (e.g. age, size, and weight) and the routes of administration have to be taken into account to determine the appropriate dosage, so as a therapeutically effective amount will be administered to the patient. In some embodiments, the effective amount of the compound of formula (I) administered to the subject is from about 1 to 100 mg/Kg body weight of the subject by intravenous, intramuscular injection or oral intake. The amount is administered to the subject by intravenous, intramuscular injection or oral intake at about 2, 3, 4, 5, 6, 7, 8, 9, 10, 20, 30, 40, 50, 60, 70, 80, 90 or 100 mg/Kg body weight of the subject. In one embodiment, the subject is human and the administration amount if the compound is about 1 to about 50 mg/Kg body weight in a human; preferably about 1 to about 30 mg/Kg body weight in a human, preferably, about 1 to about 20 mg/Kg body weight, about 1 to about 10 mg/Kg body weight, about 2 to about 10 mg/Kg body weight, about 2 to about 8 mg/Kg body weight or about 2 to about 10 mg/Kg body weight; more preferably about 3 to about 5 mg/Kg body weight. The dose can be administered in a single aliquot, or alternatively in more than one aliquot.

Generally, the compound having formula (I) of this invention is present at a level of about 0.1% to 99% by weight, based on the total weight of the pharmaceutical composition. In some embodiments, the compound having formula (I) of this invention is present at a level of at least 1% by weight, based on the total weight of the pharmaceutical composition. In certain embodiments, the compound having formula (I) is present at a level of at least 5% by weight, based on the total weight of the pharmaceutical composition. In still other embodiments, the compound having formula (I) is present at a level of at least 10% by weight, based on the total weight of the pharmaceutical composition. In still yet other embodiments, the compound having formula (I) is present at a level of at least 25% by weight, based on the total weight of the pharmaceutical composition.

Process

The present invention also relates to a process for preparing a compound of formula (I) as defined herein, said process comprising the step of:

(b) reacting a compound of formula (II) with a reducing system:

(II)

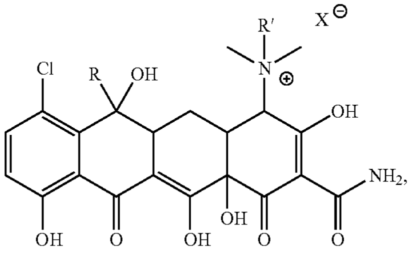

wherein R is a hydrogen atom or a methyl group,

R' is a hydrogen atom or a methyl group, and $X^-$ is an anion.

In a particular embodiment, a process for preparing a compound of formula (I):

(I)

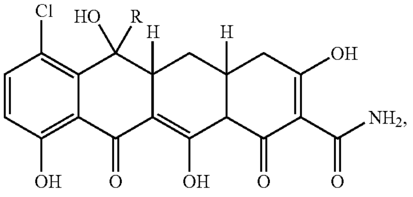

wherein R is a hydrogen atom or a methyl group, comprises the steps of:

(a) contacting a compound of formula (III) with an acid $H^+$, $X^-$ wherein $X^-$ is an anion, (III)

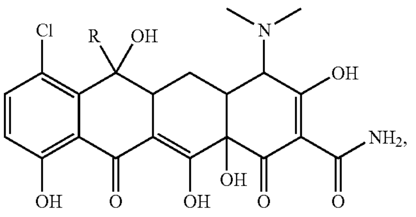

wherein R is a hydrogen atom or a methyl group, so as to obtain a compound of formula (II):

(II)

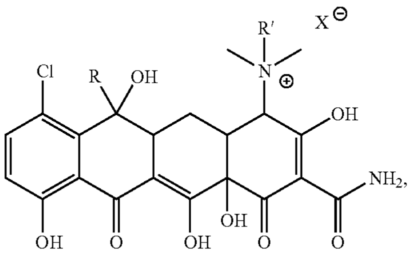

wherein R is a hydrogen atom or a methyl group,

R' is a hydrogen atom, and $X^-$ is an anion;

(b) reacting said compound of formula (II) with a reducing system.

In a particular embodiment, said steps (a) and (b) are carried out simultaneously in one-pot.

In another particular embodiment, a process for preparing a compound of formula (I):

(I)

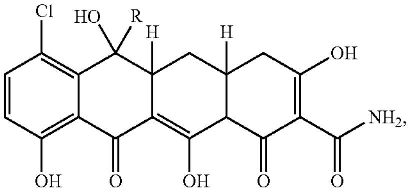

wherein R is a hydrogen atom or a methyl group, comprises the step of:

(b) reacting a compound of formula (II) with a reducing system:

(II)

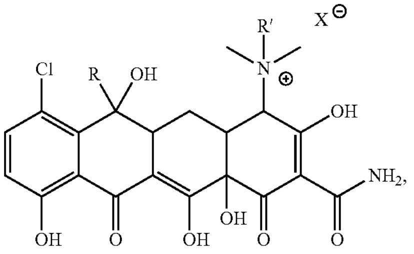

wherein R is a hydrogen atom or a methyl group,

R' is a methyl group, and $X^-$ is an anion.

The compound of formula (II) may exist in the form of, or in equilibrium with, other tautomeric (or prototropic) forms. The present invention encompasses all these forms of the compound of formula (II).

In a particular embodiment, $X^-$ is an inorganic or organic anion. Examples of inorganic anions include, but are not limited to, chloride, fluoride, bromide, iodide, tetrafluoroborate, nitrite, nitrate, sulfite, sulfate, chlorate, or perchlorate. Examples of organic anions include, but are not limited to, sulfonate (e.g. $R''SO_3^-$ with R" being a methyl, an ethyl, a phenyl, a nitrophenyl, a tolyl, $CF_3$ or $C_2F_5$) or an acetate (i.e. $R''CO_2^-$ with R" being a methyl, an ethyl, a phenyl, a nitrophenyl, a tolyl, $CF_3$ or $C_2F_5$).

As used herein, a "reducing system" refers to one or more reactants which are able to reduce a compound of formula (II). In particular, such reducing system is able to achieve a 6-dehydroxylation and 4-deamination of the compound of formula (II). As used herein, a "6-dehydroxylation" refers to a formal substitution of the hydroxy group in position 6 with a hydrogen atom. As used herein, a "4-deamination" refers to a formal substitution of the ammonium group in position 4 with a hydrogen atom. Said 6-dehydroxylation and 4-deamination are typically both carried out by using the reducing system described above, simultaneously or successively.

In a particular embodiment, the reducing system comprises a reducing metal. Examples of reducing metals include but are not limited to, reducing transition metals such as, zinc, copper, iron, silver, gold, palladium, rhodium, iridium, platinum or nickel. Preferably, the reducing metal is zinc metal. The reducing metal may be used, for instance, in the form of a metal powder.

In a particular embodiment, the reducing metal of the reducing system is combined with an acid. The term "acid", as used herein, refers to a Brønsted acid or a Lewis acid, preferably a Brønsted acid. Examples of Brønsted acid include, but are not limited to, hydrochloric acid, hydrobromic acid, hydroiodic acid, sulfuric acid, nitric acid, phosphoric acid, formic acid, acetic acid, trifluoroacetic acid, methanesulfonic acid, benzenesulfonic acid, p-toluenesulfonic acid, or a mixture thereof. A preferred acid is acetic acid. The reducing metal may be used, for instance, in the form of a substantially pure or a diluted solid or liquid.

In a particular embodiment, the reducing step (b) comprises contacting a compound of formula (II) with a reducing system. In a more particular embodiment, the reducing step (b) comprises contacting a compound of formula (II) with a reducing system comprising a reducing metal, and optionally an acid. In such an embodiment, the reducing metal and the acid can be contacted simultaneously or successively with the compound of formula (II). In a particular embodiment, the acid is used as a solvent in step (b). The amount of reducing metal may be catalytic, stoichiometric, or in excess, preferably in excess, with respect to the compound of formula (II). In particular, the amount of reducing metal may be comprised between 3 and 30 equivalents, preferably between 5 and 15 equivalents, with respect to the compound of formula (II).

Step (b) may be carried out at a temperature comprised between 0° C. and 50° C., preferably 15° C. and 35° C.

Step (b) produces a compound of formula (I). Sub-products (e.g. tetracycline derivatives which are not a compound of formula (I)) may be produced in step (b). The compound of formula (I) may be isolated and purified by any techniques well-known to the skilled artisan.

In a particular embodiment, the compound of formula (II) is of formula (2):

(2)

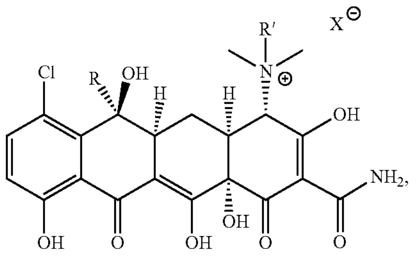

wherein R, R' and $X^-$ are as defined in formula (II).

In a particular embodiment, R' is a hydrogen atom. A compound of formula (II) wherein R' is a hydrogen atom can in particular be obtained by contacting a compound of formula (III) represented as follows, with an acid ($H^+$, $X^-$) wherein $X^-$ is as defined in formula (II):

(III)

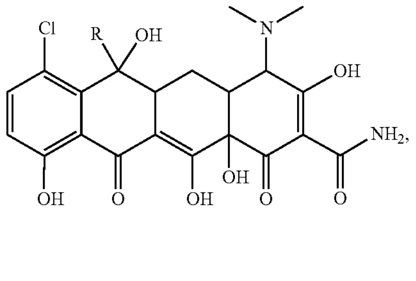

wherein R is a hydrogen atom or a methyl group.

Conditions (e.g. temperature, duration, solvents . . . ) for implementing such reaction with an acid can be judiciously chosen and tuned by the skilled artisan.

Examples of acid ($H^+$, $X^-$) (also written HX) include, but are not limited to, hydrochloric acid, hydrofluoric acid, hydrobromic acid, hydroiodic acid, tetrafluoroboric acid, nitric acid, nitrous acid, sulfuric acid, sulfurous acid, chloric acid, perchloric acid, a sulfonic acid (e.g. $R''SO_3H$ with R'' being a methyl, an ethyl, a phenyl, a nitrophenyl, a tolyl, $CF_3$ or $C_2F_5$) or a carboxylic acid (e.g. $R''CO_2H$ with R'' being a methyl, an ethyl, a phenyl, a nitrophenyl, a tolyl, $CF_3$ or $C_2F_5$).

In another particular embodiment, R' is a methyl. In such embodiment, the process of the invention may further comprise, before step (b), a step of: (a) reacting a compound of formula (III) as defined herein with a methylation agent, thereby producing a compound of formula (II) wherein R' is a methyl.

As used herein, a "methylation agent" refers to one or more reactants, which are able to release or transfer a formal electrophilic methyl (i.e. formally $CH_3^+$) to a compound of formula (III), especially to the dimethylamine group in position 4 of such a compound.

In a particular embodiment, the methylation agent is a methyl halide, such as methyl bromide or methyl iodide; a methyl sulfonate such as methyl tosylate, methyl triflate, or methyl nosylate; a mixture thereof.

Preferably the methylation agent is methyl iodide.

Conditions (e.g. temperature, duration, solvents . . . ) for the methylation step (a) can be judiciously chosen and tuned by the skilled artisan. Step (a) produces a compound of formula (II) wherein R' is a methyl. Sub-products (e.g. tetracycline derivatives which are not a compound of formula (II)) may be produced in step (a). The compound of formula (II) may be isolated and purified by any techniques well-known to the skilled artisan.

In a particular embodiment, the compound of formula (III) is of formula (3):

(3)

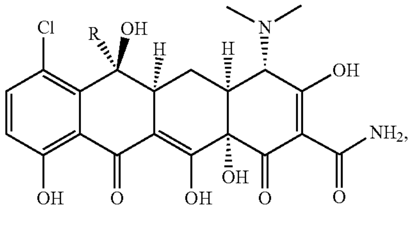

wherein R is as defined in formula (III).

In a preferred embodiment, R in formulae (II), (III), (2), or (3) is a hydrogen atom.

The invention will also be described in further detail in the following examples, which are not intended to limit the scope of this invention, as defined by the attached claims.

EXAMPLES

Example 1: Preparation of Compounds of Formula (I)

Scheme 1 Synthetic pathway for preparing compounds of formula (I)

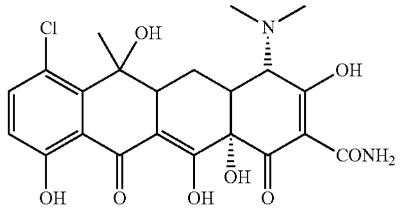

Chlortetracyclin

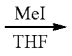

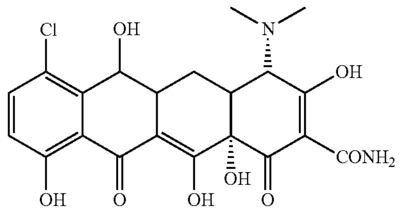

Demeclocyclin

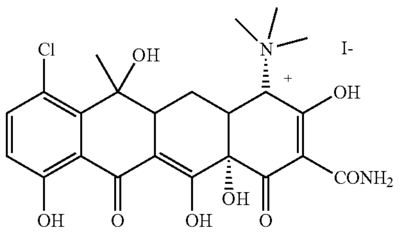

50%

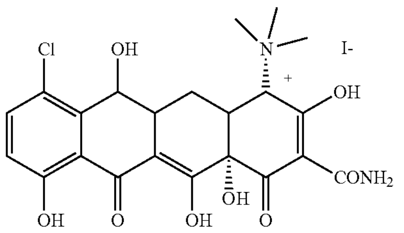

59%

-continued

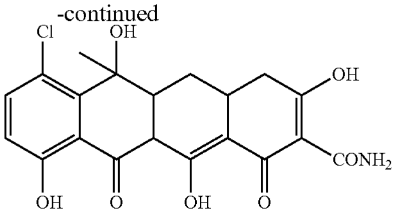

60%

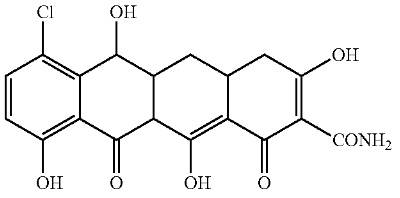

67%

7-chloro-3,6,10,12-tetrahydroxy-6-methyl-1,11-dioxo-1,4,4α,5,5α, 6,11,12α-octahydrotetracene-2-carboxamide (1-Me)

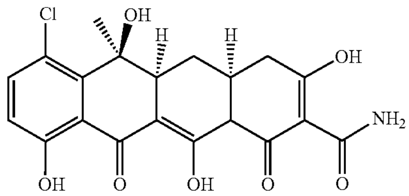 [SMILES: NC(=O)C1=C(O)C[C@@H]2C[C@H]3C(=C(O)C2C1=O)C(=O)c1c(O)ccc(Cl)c1[C@H]3O]

In a round-bottom flask, chlortetracyclin-methylammonium iodide (510 g, 1.03 mmol, 1.0 equiv.), was suspended in acetic acid (8.0 mL) and stirred at room temperature during 30 min. Zinc powder (0.598 g, 10.3 mmol, 10 equiv.) was added and the mixture was stirred for 2 hours at room temperature. The mixture was then filtered on a celite pad and rinsed with a little bit of AcOH and then with dichloromethane. The filtrate was then transferred in a separating funnel and washed with an aqueous solution of HCl 1M, then extracted 2 times with dichloromethane. The organic phases were then dried on $NaSO_4$, filtered and concentrated under reduced pressure. The oil thus obtained was diluted with the smallest amount possible of EtOAc, and then precipitated using petroleum ether. The desired compound was obtained as a yellow powder (270 mg, 60% yield).

$^1$H NMR (300 MHz, DMSO-D6) δ 15.21 (s, 1H), 12.25 (s, 1H), 9.06-8.61 (m, 2H), 7.53 (d, J=8.9 Hz, 1H), 6.98-6.89 (m, 1H), 6.67 (s, 1H), 5.28 (s, 1H), 3.16 (dd, J=14.6, 5.1 Hz, 1H), 2.86 (dd, J=10.9, 5.3 Hz, 1H), 2.42-2.15 (m, 3H), 1.81 (s, 3H), 1.09 (t, J=7.0 Hz, 1H), 0.85 (q, J=8.2, 7.0 Hz, 1H).

$^{13}$C NMR (75 MHz, DMSO-D6) δ 194.93, 189.73, 173.54, 160.71, 143.76, 139.49, 121.34, 118.77, 118.13, 117.06, 70.46, 64.88, 50.69, 46.55, 42.27, 35.53, 30.08, 26.67, 24.82, 15.13.

HRMS: m/z calculated for $C_{20}H_{19}ClNO_7$ ($[M+H]^+$): 420.0845; found: 420.0850.

7-chloro-3,6,10,12-tetrahydroxy-1,11-dioxo-1,4,4α,5,5α,6,11,12α-octahydrotetracene-2-carboxamide (1-H)

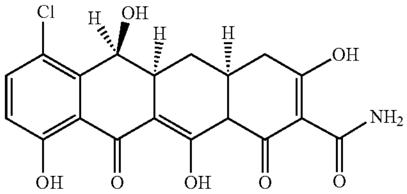

In a round-bottom flask, demeclocyclin-methylammonium iodide (50 mg, 0.10 mmol, 1.0 equiv.) was suspended in acetic acid (5.0 mL) and stirred at rt during 30 min. Then zinc powder (0.07 g, 1.3 mmol, 10 equiv.) was added and the mixture was stirred for 2 hours at rt. The mixture was then filtered on a celite pad and rinsed with a little bit of AcOH and then with dichloromethane. The filtrate was then transferred in a separating funnel and washed with an aqueous solution of HCl 1M, then extracted 2 times with dichloromethane. The organic phases were then dried on $NaSO_4$, filtered and concentrated under reduced pressure. The oil thus obtained was diluted with a minimum amount of EtOAc, and then precipitated using petroleum ether. The desired compound was obtained as a yellow powder (26 mg, 67% yield).

$^1$H NMR (300 MHz, DMSO-D6) δ 14.71 (s, 1H), 11.92 (s, 1H), 8.94 (d, 2H), 7.60 (d, J=9.0 Hz, 1H), 6.96 (d, J=8.9 Hz, 1H), 4.70 (d, J=2.40 Hz, 1H), 3.74-3.10 (m, 5H), 2.87-2.73 (m, 1H), 1.99 (s, 1H), 1.87 (q, J=12.3 Hz, 1H), 1.70 (m, 1H), 1.18 (t, J=7.1 Hz, 1H).

$^{13}$C NMR (75 MHz, DMSO-D6) δ 195.35, 194.86, 191.74, 173.24, 160.12, 140.86, 136.61, 122.17, 118.73, 116.01, 63.90, 59.72, 50.96, 50.94, 37.96, 29.05, 26.64, 20.72, 14.05.

HRMS: m/z calculated for $C_{19}H_{16}ClNO_7$ ($[M+H]^+$): 406.0694; found: 406.0696.

Example 2: Biological Evaluation of Compounds of Formula (I)

Thioflavin-T Fluorescence Assay

Aggregation studies were performed at 37° C. on samples containing 70 μM human recombinant monomeric α-Synuclein that were submitted to constant orbital agitation (Thermomixer Comfort, Eppendorf) at 600 rpm in the absence or in the presence of test compounds, at 100 μM. The formation of α-Synuclein aggregated species was monitored using the fluorescence probe Thioflavin-T (LeVine, Methods Enzymol. 1999, 309, 274-284; González-Lizárraga, et al. Sci Rep. 2017, 7, 41755), at a concentration of 25 μM. Changes in emission fluorescence were measured after 144 hrs of continuous shaking, at an excitation wavelength of 450 nm using a Horiba FluoroMax 4 spectrometer.

FIG. 1 shows that amyloid aggregation (i.e., Thioflavin-T fluorescence) is increased in tetracycline-free α-Synuclein samples undergoing continuous orbital shaking for 144 hours. The reference tetracycline DOX (100 μM), substantially reduces α-Synuclein aggregation but compounds of the invention (1-Me) (100 μM) and (1-H) (100 μM) show a higher efficacy than DOX. More specifically, residual Thiofavin-T fluorescence levels of 21.1%, 13.5% and 1.5% were obtained with DOX, 1-Me and 1-H respectively after 144 hours.

Inhibition of Bacterial Growth

The antibacterial activities of test compounds were evaluated using the disc diffusion method (Kavanagh, Academic Press, Inc., New York, 1963, 125-140; Pomares et al, J Bacteriol. 2008, 190, 4328-4334). Briefly, filter-paper discs impregnated with 10 μl of two-fold serial dilutions of test compounds were placed onto LB solid medium Petri dishes. Then, aliquots (50 μl) of an *E. coli* DH5α culture in stationary phase were mixed with 3 ml of top agar (0.7% agar) and overlaid onto the plates. After overnight incubation at 37° C., the plates were examined for different degrees of inhibition. The antibacterial efficacy of a test compound was estimated by the Minimum Inhibitory Concentration (MIC) assay that determines the lowest concentration inhibiting visible growth of bacteria. Each test was performed in duplicate vs. the reference compound, doxycycline ("DOX").

Table 1 below compares the antimicrobial activities of the compounds of the invention (1-Me) and (1-H) with respect to that of the reference tetracycline DOX. The test was carried out with *E. coli* DH5α Gram negative bacteria. Bacterial growth inhibition by DOX is signified by a MIC value of 62.5 μM. (1-Me) and (1-H) failed to inhibit bacterial growth up to 2000 μM. Each compound was assayed twice.

TABLE 1

Disc diffusion assay to assess antimicrobial activities

| Test compounds | Minimal inhibitory concentration (μM) |
|---|---|
| DOX | 62.5 |
| (1-Me) | >2000 |
| (1-H) | >2000 |

Example 3: Concentration-Dependent Neuroprotective Effects

The inventors have further shown that compounds 1-H and 1-Me exert robust and concentration-dependent neuroprotective effects in a cell model in which the dopaminergic midbrain neurons, vulnerable in Parkinson's disease, degenerate further to a spontaneous oxidative stress of low intensity resulting from the presence of catalytic iron in the culture medium (Guerreiro et al, J Neurochem. 2009; 109 (4):1118-28; Rousseau et al, Mol Pharmacol. 2013; 84(6): 888-98).

Methods

Primary Cultures of Mouse Midbrain

Cultures were carried out using embryos of Swiss mice (Janvier LABS, Le Genest St. Isles, France), collected at 13.5 days of gestation. The experimental procedures were performed in accordance with Directive 2010/63/EU of the Council of the European Union, using a protocol validated by the Charles Darwin ethics committee no. 5. The protocol is based on techniques reported previously (Rousseau et al, 2013, supra; Lavaur et al, J Neurochem. 2017; 142(1):14-28), using an additional step of trypsinization with an EDTA (2 mM)-trypsin (0.05%) solution to facilitate the dissociation of brain tissue. The cells in suspension are distributed in 48-well multi-well dishes (Nunc; ThermoFisher Scientific), at a density of $50\text{-}80.10^3$ cells/cm$^2$, using Dulbecco's Modified Eagle's Medium/Nutrient Mixture F-12 Ham (Sigma- Aldrich), supplemented with 10% fetal calf serum. After 2 hours, the cultures are washed completely and placed in the presence of the same medium containing only 20 μg/ml of bovine insulin. The cultures are also treated with cytarabine (1.5 μM) on the first day in vitro and on the following day to reduce the number of glial cells in the cultures.

These cultures contain between 1 to 2% of dopaminergic neurons. The presence of these neurons is revealed by tyrosine hydroxylase (TH) immunocytochemistry, using an immunofluorescence protocol described previously (Lavaur et al, 2017, supra). Assessment of the number of dopaminergic neurons is done by counting $TH^+$ neurons with a Nikon Eclipse Ti-U inverted microscope.

The reference molecule used to prevent the loss of dopaminergic neurons is apotransferrin (APO; Sigma Aldrich; 100 μg/ml), a protein that chelates ferric iron in culture medium.

Results

Figure 2:
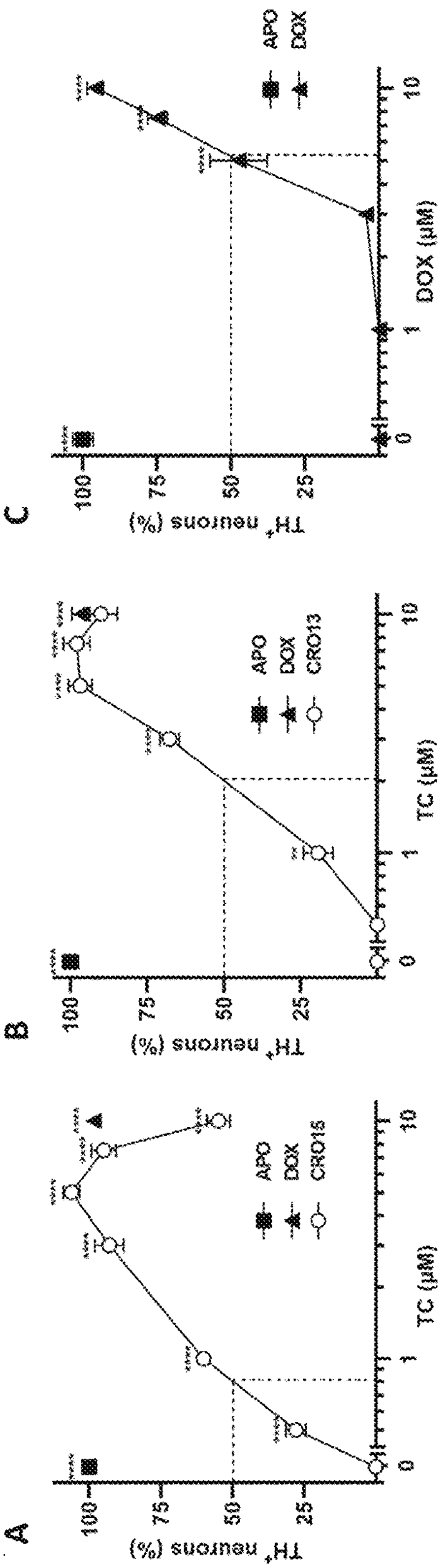
FIG. 2: Neuroprotective effects of compounds (1-Me), (1-H) and doxycycline (DOX) on dopaminergic neurons. Measurement of the survival of the TH+dopaminergic neurons in cultures of the midbrain of mice, cultured for 7 days, in the presence or absence of increasing concentrations of the compounds (1-Me) (A), (1-H) (B) or DOX (C). DOX is used at 10 μM only in graphs (A) and (B). Apotransferrin (APO; 100 μg/ml) is used as a reference neuroprotective molecule. p<0.01 and **p<0.0001 vs. controls (n=6-12/experimental point). One-way ANOVA followed by Dunnett's post-hoc test. The EC50s are estimated graphically over all the experimental points for each compound. Experimental data comes from at least 3 independent experiments. TC: tetracycline.

As shown on FIG. 2, compound 1-H turns out to be even more powerful than Compound 1-Me which itself is more powerful than DOX, when referring to the $EC_{50_s}$ (concentrations protecting 50% of TH+neurons) of the 3 tetracyclines, estimated at 0.81 μM, 2.01 μM and 5.2 μM respectively.

The invention claimed is:

1. A method of treating a neurodegenerative or neuroinflammatory disease comprising administering a compound represented by the following formula (I):

(I)

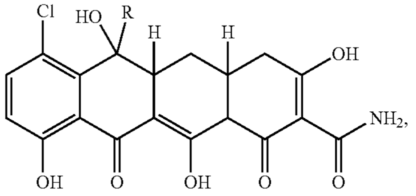

wherein R is a hydrogen atom or a methyl group, or a pharmaceutically acceptable salt or solvate thereof, to a subject in need of treatment.

2. The method according to claim 1, wherein said neurodegenerative or neuroinflammatory disease is a synucleinopathy.

3. The method according to claim 1, wherein said neurodegenerative or neuroinflammatory disease is a synucleinopathy selected from the group consisting of Parkinson's disease, diffuse Lewy body disease, and multiple system atrophy.

4. The method according to claim 1, wherein said compound is of formula (1):

(1)

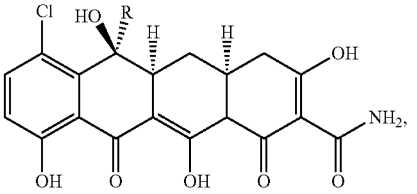

wherein R is a hydrogen atom or a methyl group.

5. The method according to claim 1, wherein said compound is administered as a pharmaceutical composition comprising a compound of formula (I) and at least one pharmaceutically acceptable excipient.

6. A pharmaceutical composition comprising a compound of formula (I-H):

(I-H)

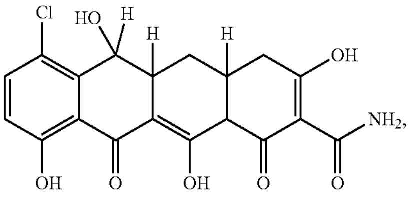

or a pharmaceutically acceptable salt or solvate thereof, and at least one pharmaceutically acceptable excipient.

7. The pharmaceutical composition according to claim 6, wherein the compound of formula (I-H) is of formula (1-H):

(1-H)

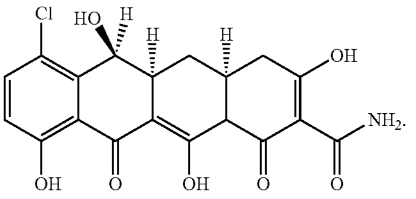

8. A process for preparing a compound of formula (I):

(I)

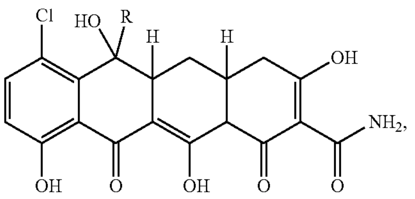

wherein R is a hydrogen atom or a methyl group, said process comprising the steps of:

(a) contacting a compound of formula (III) with an acid $H^+$, $X^-$ wherein $X^-$ is an anion, (III)

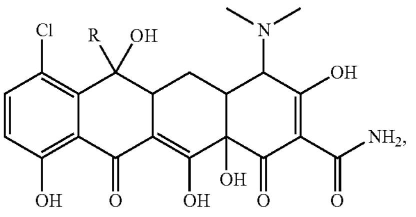

wherein R is a hydrogen atom or a methyl group, so as to obtain a compound of formula (II):

(II)

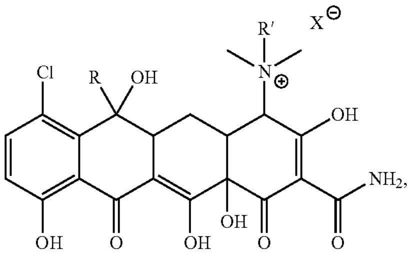

wherein R is a hydrogen atom or a methyl group,

R' is a hydrogen atom, and $X^-$ is an anion;

(b) reacting said compound of formula (II) with a reducing system.

9. The process according to claim 8, wherein the reducing system comprises a reducing metal and optionally an acid.

10. A process for preparing a compound of formula (I):

(I)

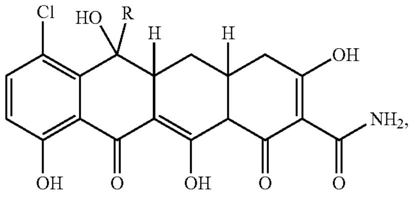

wherein R is a hydrogen atom or a methyl group, said process comprising the step of:

(a) reacting a compound of formula (II) with a reducing system:

(II)

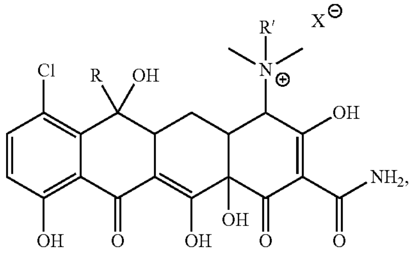

wherein R is a hydrogen atom or a methyl group,

R' is a methyl group, and $X^-$ is an anion.

11. The process according to claim 10, wherein the reducing system comprises a reducing metal and optionally an acid.

12. The process according to claim 10, wherein said process further comprises, before step (a):

reacting a compound of formula (III) with a methylation agent:

(III)

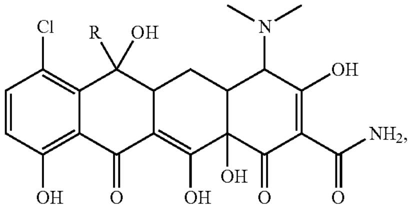

wherein R is a hydrogen atom or a methyl group, thereby producing a compound of formula (II) wherein R' is a methyl.

13. The process according to claim 12, wherein said methylation agent is a methyl halide; a methyl sulfonate; or a mixture thereof.

14. The process according to claim 13, wherein said methyl halide is methyl bromide or methyl iodide; said methyl sulfonate is methyl tosylate or methyl nosylate.

* * * * *